United States Patent [19]

Beller et al.

[11] Patent Number: 5,744,643
[45] Date of Patent: Apr. 28, 1998

[54] PROCESS FOR PREPARING AROMATIC AMINES

[75] Inventors: Matthias Beller, Idstein; Ahmed Tafesh, Kelkheim, both of Germany; Christian Kohlpaintner, Corpus Christi, Tex.; Christoph Naumann, Niedernhausen, Germany

[73] Assignee: Hoechst Aktiengesellschaft, Frankfurt am Main, Germany

[21] Appl. No.: 604,572

[22] Filed: Feb. 21, 1996

[30] Foreign Application Priority Data

Feb. 23, 1995 [DE] Germany .................. 195 06 278.7

[51] Int. Cl.⁶ .................................................. C07C 209/36
[52] U.S. Cl. .................. 564/417; 564/418; 564/420; 564/423
[58] Field of Search .................. 564/417, 418, 564/420, 423

[56] References Cited

U.S. PATENT DOCUMENTS 4,120,901 10/1978 Hobbs et al. .................. 260/585 D
5,105,012 4/1992 Theodoridis .................. 564/417
5,411,973 5/1995 Russell et al. .................. 514/347

FOREIGN PATENT DOCUMENTS 362037 4/1990 European Pat. Off. .
369864 5/1990 European Pat. Off. .
92/06067 4/1992 WIPO .

OTHER PUBLICATIONS

Journal of Natural Gas Chemistry, Bd. 4, Nr. 4, Apr. 1995, pp. 393–399, XP 000195871 Xia Chun–Gu "Ruthenium–T-PPTS catalyzed reduction of nitrobenzene to aniline".

Journal of the Chemical Society, Chemical Communications, 1994 Letchworth GB, pp. 863–864, XP 000195897 Nagavelli P. "Palladium Complex–Potassium Carbonate–catalysed Reductive Carbonylation of Mono– and Di–nitroaromatic Compounds".

*Primary Examiner*—Brian M. Burn
*Attorney, Agent, or Firm*—Connolly & Hutz

[57] ABSTRACT

The present invention relates to a process for preparing aromatic amines by reacting an aromatic nitro compound with carbon monoxide in a solvent mixture comprising water and a water-insoluble organic solvent by means of a catalyst comprising palladium and a water-soluble phosphine under a pressure of from 5 to 300 bar and at a temperature of from 50 to 200° C., and separating the aqueous phase and the organic phase.

22 Claims, No Drawings

PROCESS FOR PREPARING AROMATIC AMINES

The present invention relates to a process for preparing aromatic amines which is improved in comparison with the prior art. A frequently used route for preparing aromatic amines is hydrogenation of aromatic nitro compounds using supported catalysts containing, for example, nickel or palladium. In this process, the supported catalyst is used either arranged as a fixed bed or in the form of a slurry (suspension). A disadvantage in the use of supported catalysts arranged as a fixed bed is that carrying out this process is tied to specific reaction vessels, for example tube reactors having an internal cooling system. If the supported catalyst is used as a slurry, problems arise in the controlled removal of heat during the reaction and, in addition, the supported catalyst has to be removed after the reaction is complete, for example by means of a complicated filtration.

In carrying out these two processes, care always has to be taken to ensure that catalyst residues, caused by abrasion of the catalyst arranged as a fixed bed or by insufficient filtration of the catalyst slurry, do not get into the reaction product. It is known that even very small amounts of the supported catalysts can lead to problems in the further processing of the reaction products.

Furthermore, both palladium and nickel supported catalysts leave something to be desired in respect of the selectivity of the hydrogenation of aromatic compounds. For a series of sensitive substituents they lead to undesired reactions by either cleaving off or hydrogenating these substituents.

J. Chem. Soc., Chem. Commun., 1994, pages 863 to 864, describes a process for the reductive carbonylation of aromatic mononitro and dinitro compounds. The aromatic mononitro and dinitro compounds can be reacted with carbon monoxide in a benzene/methanol mixture in the presence of catalytic amounts of 1,3-bis (diphenylphosphino)propanepalladium dichloride and potassium carbonate to form urethanes. The reaction gives the desired urethanes (carbamates) as main product. Amines and possibly azo and azoxy compounds are formed in addition. The process appears relatively unsuitable for preparation of amines, since the maximum amine yield when using p-nitroanisole as starting material is only 40%. In all other cases the amine yield is even lower, as shown in Table 1.

There is therefore a need to provide a process for preparing aromatic a mines which avoids the abovementioned disadvantages and can be carried out in a simple manner. Furthermore, the process should make accessible not only the usual aromatic amines but also those aromatic amines which have sensitive substituents.

This object is surprisingly achieved by the process of the present invention for preparing aromatic amines. It comprises reacting an aromatic nitro compound with carbon monoxide in a solvent mixture comprising water and a water-insoluble organic solvent by means of a catalyst comprising palladium and a water-soluble phosphine under a pressure of from 5 to 300 bar and at a temperature of from 50 to 200° C., and separating the aqueous phase and the organic phase.

The process of the present invention has a number of advantages. On the one hand, it is not tied to the use of specific reaction vessels (tube reactors having internal cooling) and, on the other hand, avoids a time-consuming and complicated separation of the catalyst after the reaction is complete. It should be pointed out at this juncture that the supported catalyst separated off by filtration is in a highly active form and therefore has to be handled with special care. These difficulties do not occur when carrying out the process of the present invention, since the catalyst comprising palladium and a water-soluble phosphine is present as a solution in water and can be removed from the reaction mixture by simple separation of the aqueous phase. The aqueous, catalyst-containing phase can subsequently be reused in the reaction without special protective measures being necessary for handling the aqueous solution containing the active catalyst.

Furthermore, the removal of the heat of reaction liberated during the reaction of the present invention presents no problems, since the reaction proceeds in the presence of a heat buffer having a particularly high heat capacity, namely water, and, in addition, excess heat is effectively conducted away by vaporization of water. The problem of temperature control is also simplified because the amount of heat liberated in the reduction of the aromatic nitro compound by means of CO with formation of $CO_2$ is less than the amount of heat formed in a catalytic hydrogenation of an aromatic nitro compound with formation of water.

The process of the present invention is notable for being able to be applied to any aromatic nitro compounds which can also contain a plurality of nitro groups.

The aromatic nitro compound used is usually a compound of the formula $R^1R^2R^3ArNO_2$, where $R^1$, $R^2$, $R^3$ are identical or different and are each hydrogen, an alkyl or alkoxy radical having from 1 to 6 carbon atoms, a halogenated alkyl radical having from 1 to 4 carbon atoms, a halogen, —OH, —CHO, —CO—$R^4$, —$CO_2R^4$, —CONH$R^4$, —CON($R^4$)$_2$, —S$R^4$, where $R^4$ is a radical having from 1 to 6 carbon atoms, —CN or —CH=CH—$R^5$, where $R^5$ is hydrogen or a radical having from 1 to 6 carbon atoms, and Ar is an aromatic radical.

In a number of cases, the aromatic nitro compound used is a compound $R^1R^2R^3ArNO_2$, where $R^1$, $R^2$ and $R^3$ are hydrogen, an alkyl or alkoxy radical having from 1 to 4 carbon atoms, a halogenated alkyl radical having 1 or 2 carbon atoms, a halogen, —OH, —CO—$R^4$, —CN or —CH=CH—$R^5$.

Halogen, —OH, —CO—$R^4$, —CN and —CH=CH—$R^5$ are problem substituents which are either cleaved off or reduced in the course of catalytic hydrogenation or, in the case of the OH group, have a deactivating action. If the preparation of aromatic amines having one or more of these substituents is intended, the aromatic nitro compound used is a compound $R^1R^2R^3ArNO_2$, where at least one of the radicals $R^1$, $R^2$ and $R^3$ is a halogen, —OH, —CO—$R^4$, —CN or —CH=CH—$R^5$, or one or two of the radicals $R^1$, $R^2$ and $R^3$ is a halogen, —OH, —CO—$R^4$, —CN or —CH=CH—$R^5$, and, in particular, one or two of the radicals $R^1$, $R^2$ and $R^3$ are —Cl, —Br, —OH, —CO—$R^4$, where $R^4$ is an alkyl radical having from 1 to 4 carbon atoms or a phenyl radical, —CN or —CH=CH—$R^5$, where $R^5$ is hydrogen, an alkyl radical having from 1 to 4 carbon atoms or a phenyl radical.

The aromatic nitro compound used is a compound $R^1R^2R^3ArNO_2$, where Ar is an aromatic radical having from 6 to 20 carbon atoms, in particular a phenyl, naphthyl, phenanthryl, biphenyl or binaphthyl radical, preferably a phenyl, naphthyl or biphenyl radical, particularly preferably a phenyl radical.

The reaction takes place in a 2-phase system which comprises water as one phase and a water-insoluble organic solvent as the other phase. The water-insoluble organic solvent used is an aromatic hydrocarbon, an aliphatic hydrocarbon, a chlorinated aromatic or aliphatic hydrocarbon or a mixture thereof, for example toluene, ortho-xylene, meta-xylene, para-xylene, mixtures of isomeric xylenes, ethylbenzene, mesitylene, chlorotoluene, chlorobenzene, dichlorobenzene or mixtures of the above solvents.

The catalyst required for carrying out the reaction comprises palladium and a water-soluble phosphine. Palladium is usually used in the form of a water-soluble palladium salt, in particular palladium chloride, palladium nitrate, palladium acetate or palladium sulfate.

In carrying out the process, one is not tied to a certain ratio of palladium to phosphine. Palladium and the water-soluble phosphine can usually be used in a molar ratio of from 1:0.2 to 1:100, in particular from 1:1 to 1:50, preferably from 1:2 to 1:20.

If a water-soluble diphosphine is used, it is generally sufficient to use palladium and the diphosphine in a molar ratio of from 1:1 to 1:10, in particular from 1:2 to 1:6.

If a water-soluble monophosphine is used, it is in most cases sufficient to use palladium and the monophosphine in a molar ratio of from 1:2 to 1:20, in particular from 1:4 to 1:12.

A well-suited water-soluble phosphine is a phosphine and/or diphosphine containing —$SO_3M$ groups, where M is hydrogen, ammonium, a monovalent metal or the equivalent of a polyvalent metal, in particular ammonium or an alkali metal, preferably sodium or potassium, particularly preferably sodium. Mixtures of various phosphines or mixtures of phosphines having a different degree of sulfonation can also be used with good results.

In a number of cases it has been found to be useful to use a triarylphosphine containing from 1 to 6, in particular from 1 to 3, —$SO_3M$ groups, where the aryl radicals are identical or different and are each phenyl or naphthyl, or a mixture of such triarylphosphines, in particular a comparatively readily available triphenylphosphine containing from 1 to 3 —$SO_3M$ groups.

Good results can be achieved by using, as water-soluble phosphine, a phosphine of the formula (A)

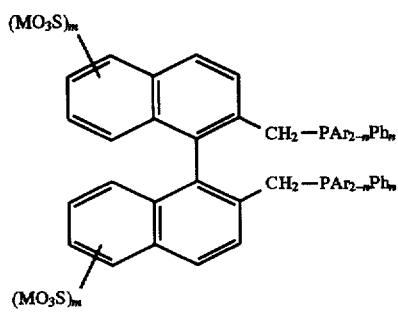

(A)

where Ar is m-$C_6H_4SO_3M$, M is hydrogen, ammonium, a monovalent metal or the equivalent of a polyvalent metal and Ph is a phenyl radical, m are identical or different and each have the value 1 or 2 and n are identical or different and are each 0, 1 or 2, or a mixture of such phosphines.

The process of the present invention can be carried out with particularly good results by using, as water-soluble phosphine, a phosphine of the formula (B)

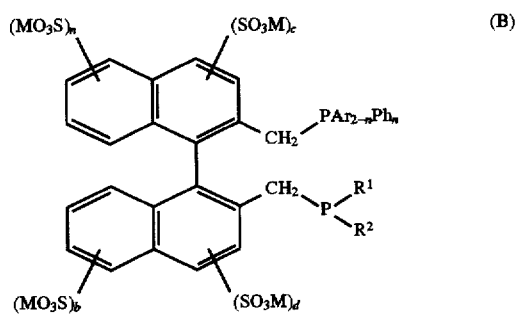

(B)

where M is hydrogen, ammonium, a monovalent metal or the equivalent of a polyvalent metal, a, b, c and d are each 0 or 1, with the proviso that a+b+c+d is an integer from 1 to 4, Ar is a m-($MSO_3$)-$C_6H_4$ radical and M is as defined above, n is 0, 1 or 2, Ph is a phenyl radical $R^1$ and $R^2$ are identical or different and are each an alkyl radical having from 1 to 10 carbon atoms or a cycloaliphatic radical having from 5 to 10 carbon atoms in the ring, or a mixture of such phosphines.

Owing to their good suitability, special mention should be made of phosphines of the formula (B) in which $R^1$ and $R^2$ are each a cyclohexyl radical. Mixtures of these phosphines can also be used.

It may be mentioned at this point that the phosphines of the formula (B) are new phosphines. These phosphines and their preparation are subject matter of a German Patent Application (file number 195 06 279.5) filed on the same day as the present patent application.

The process can also be carried out at a pressure of <5 bar and a pressure of >300 bar. Pressures below 5 bar significantly increase the reaction time, pressures above 300 bar usually require appropriately designed pressure reactors.

In most cases, a pressure of from 10 to 200 bar, in particular from 50 to 150 bar, has been found to be sufficient.

The process can also be carried out at temperatures of <50° C., but in this case significantly increased reaction times have to be accepted. Temperatures of >200° C. lead to considerable acceleration of the reaction, and the formation of by-products can be favored too. The process is usually carried out at from 70 to 160° C., in particular from 80 to 150° C. These temperature ranges have been found to be sufficient for many cases.

After the reaction is complete, the reaction mixture is cooled and depressurized. The organic phase containing the desired product and the aqueous phase containing the catalyst are subsequently separated from one another. The ready separability of the catalyst is an advantage of the process, since complicated separation and recovery of the catalyst is not necessary. The aqueous phase separated off can, if desired after addition of palladium and/or water-soluble phosphine, be reused in the reaction.

The present invention also provides new catalysts suitable for carrying out the process, which catalysts contain palladium and the phosphine of the formula (B) in a molar ratio of from 1:1 to 1:10, in particular from 1:2 to 1:6. The catalysts contain palladium and, in particular, the phosphine of the formula (B) in which $R^1$ and $R^2$ are each a cyclohexyl radical in a molar ratio of from 1:1 to 1:10, in particular from 1:2 to 1:6.

To carry out the process, the individual components of the catalyst, namely the palladium, for example in the form of a water-soluble salt, and the water-soluble phosphine can be used in the reaction.

If desired, the catalyst can be prepared beforehand by combining a water-soluble Pd salt and the water-soluble phosphine in aqueous solution and can be used in the process as aqueous solution or in isolated form.

The following examples illustrate the invention without restricting it.

EXPERIMENTAL PART

EXAMPLE 1a
Preparation of 4-chloro-3-aminoacetophenone

A degassed solution of 40 mmol of 4-chloro-3-nitroacetophenone (starting material) and 60 ml of xylene are placed in an autoclave (volume: 200 ml). 5 mmol of TPPTS (in the form of 9.2 g of an aqueous solution containing 0.546 mol of TPPTS/kg of solution) as phosphine and 2.4 g (60 mmol) of NaOH, 23.8 ml of $H_2O$ and 1.0 mmol of $PdCl_2$ are added. The pH is from 10.5 to 11.0.

The autoclave is closed, evacuated and filled with nitrogen. The evacuation and filling with nitrogen is repeated twice, then the autoclave is filled with CO, evacuated and refilled with CO. The evacuation and filling with CO is repeated twice.

The autoclave is subsequently pressurized with CO to a pressure of 120 bar and the mixture is heated to 100° C. while stirring. The reaction time is 20 hours. The mixture is subsequently cooled to room temperature, the autoclave is emptied and the organic phase is separated from the aqueous phase. The organic phase is filtered to remove traces of palladium and evaporated under reduced pressure, with the desired product being purified, if desired by crystallization or chromatography.

EXAMPLE 1b
Preparation of 4-chloro-3-aminoacetophenone

A degassed solution of 40 mmol of 4-chloro-3-nitroacetophenone (starting material) and 60 ml of xylene are placed in an autoclave (volume: 200 ml). 2.5 mmol of BINAS (in the form of 14.4 g of an aqueous solution containing 0.173 mol of BINAS/kg of solution) as phosphine and 2.4 g (60 mmol) of NaOH, 23.8 ml of $H_2O$ and 1.0 mmol of $PdCl_2$ are added. The pH is from 10.5 to 11.0.

The autoclave is closed, evacuated and filled with nitrogen. The evacuation and filling with nitrogen is repeated twice, then the autoclave is filled with CO, evacuated and refilled with CO. The evacuation and filling with CO is repeated twice.

The autoclave is subsequently pressurized with CO to a pressure of 120 bar and the mixture is heated to 90° C. while stirring. The reaction time is 20 hours. The mixture is subsequently cooled to room temperature, the autoclave is emptied and the organic phase is separated from the aqueous phase. The organic phase is filtered to remove traces of palladium and evaporated under reduced pressure, with the desired product being purified, if desired by crystallization or chromatography.

EXAMPLE 2a
Preparation of 2-chloro-5-trifluoromethylaniline

A degassed solution of 40 mmol of 2-chloro-5-trifluoromethylnitrobenzene (starting material) and 40 ml of xylene are placed in an autoclave (volume: 200 ml). 5.0 mmol of TPPTS (in the form of 9.2 g of an aqueous solution containing 0.546 mol of TPPTS/kg of solution) as phosphine and 2.4 g (60 mmol) of NaOH, 23.8 ml of $H_2O$ and 1.0 mmol of $PdCl_2$ are added. The pH is from 10.5 to 11.0.

The autoclave is closed, evacuated and filled with nitrogen. The evacuation and filling with nitrogen is repeated twice, then the autoclave is filled with CO, evacuated and refilled with CO. The evacuation and filling with CO is repeated twice.

The autoclave is subsequently pressurized with CO to a pressure of 120 bar and the mixture is heated to 100° C. while stirring. The reaction time is 20 hours. The mixture is subsequently cooled to room temperature, the autoclave is emptied and the organic phase is separated from the aqueous phase. The organic phase is filtered to remove traces of palladium and evaporated under reduced pressure, with the desired product being purified, if desired by crystallization or chromatography.

EXAMPLE 2b
Preparation of 2-chloro-5-trifluoromethylaniline

A degassed solution of 40 mmol of 2-chloro-5-trifluoromethylnitrobenzene (starting material) and 40 ml of xylene are placed in an autoclave (volume: 200 ml). 3.0 mmol of BINAS (in the form of 17.3 g of an aqueous solution containing 0.173 mol of BINAS/kg of solution) as phosphine and 2.4 g (60 mmol) of NaOH, 23.8 ml of $H_2O$ and 1.0 mmol of $PdCl_2$ are added. The pH is from 10.5 to 11.0.

The subsequent procedure is as described in Example 2a.

EXAMPLE 3a
Preparation of 4-chloro-3-aminobenzonitrile

A degassed solution of 40 mmol of 4-chloro-3-nitrobenzonitrile (starting material) and 40 ml of xylene are placed in an autoclave (volume: 200 ml). 5.0 mmol of TPPTS (in the form of 9.2 g of an aqueous solution containing 0.546 mol of TPPTS/kg of solution) as phosphine and 2.4 g (60 mmol) of NaOH, 23.8 ml of $H_2O$ and 1.0 mmol of $PdCl_2$ are added. The pH is from 10.5 to 11.0.

The autoclave is closed, evacuated and filled with nitrogen. The evacuation and filling with nitrogen is repeated twice, then the autoclave is filled with CO, evacuated and refilled with CO. The evacuation and filling with CO is repeated twice.

The autoclave is subsequently pressurized with CO to a pressure of 120 bar and the mixture is heated to 100° C. while stirring. The reaction time is 20 hours. The mixture is subsequently cooled to room temperature, the autoclave is emptied and the organic phase is separated from the aqueous phase. The organic phase is filtered to remove traces of palladium and evaporated under reduced pressure, with the desired product being purified, if desired by crystallization or chromatography.

EXAMPLE 3b
Preparation of 4-chloro-3-aminobenzonitrile

A degassed solution of 40 mmol of 4-chloro-3-nitrobenzonitrile (starting material) and 40 ml of xylene are placed in an autoclave (volume: 200 ml). 2.5 mmol of BINAS (in the form of 14.4 g of an aqueous solution containing 0.173 mol of BINAS/kg of solution) as phosphine and 2.4 g (60 mmol) of NaOH, 23.8 ml of $H_2O$ and 1.0 mmol of $PdCl_2$ are added. The pH is from 10.5 to 11.0.

The subsequent procedure is as described in Example 3a.

EXAMPLE 4a
Preparation of 4-chloroaniline

A degassed solution of 40 mmol of 4-chloronitrobenzene (starting material) and 40 ml of xylene are placed in an autoclave (volume: 200 ml). 5.0 mmol of TPPTS (in the form of 9.2 g of an aqueous solution containing 0.546 mol of TPPTS/kg of solution) as phosphine and 2.4 g (60 mmol) of NaOH, 23.8 ml of $H_2O$ and 1.0 mmol of $PdCl_2$ are added. The pH is from 10.5 to 11.0.

The autoclave is closed, evacuated and filled with nitrogen. The evacuation and filling with nitrogen is repeated twice, then the autoclave is filled with CO, evacuated and refilled with CO. The evacuation and filling with CO is repeated twice.

The autoclave is subsequently pressurized with CO to a pressure of 120 bar and the mixture is heated to 100° C. while stirring. The reaction time is 20 hours. The mixture is subsequently cooled to room temperature, the autoclave is emptied and the organic phase is separated from the aqueous phase. The organic phase is filtered to remove traces of palladium and evaporated under reduced pressure, with the desired product being purified, if desired by crystallization or chromatography.

EXAMPLE 4b

Preparation of 4-chloroaniline

A degassed solution of 35 mmol of 4-chloronitrobenzene (starting material) and 40 ml of xylene are placed in an autoclave (volume: 200 ml). 2.57 mmol of BINAS (in the form of 14.85 g of an aqueous solution containing 0.173 mol of BINAS/kg of solution) as phosphine and 2.4 g (60 mmol) of NaOH, 22.0 ml of H$_2$O and 0.85 mmol of PdCl$_2$ are added. The pH is from 10.5 to 11.0.

The subsequent procedure is as described in Example 4a.

EXAMPLE 5a

Preparation of 5-chloro-2-hydroxyaniline

A degassed solution of 10 mmol of 5-chloro-2-hydroxynitrobenzene (starting material) and 40 ml of xylene are placed in an autoclave (volume: 200 ml). 0.25 mmol of TPPTS (in the form of 4.6 g of an aqueous solution containing 0.546 mol of TPPTS/kg of solution) as phosphine and 0.6 g (15 mmol) of NaOH, 41 ml of H$_2$O and 0.25 mmol of PdCl$_2$ are added. The pH is from 10 to 10.5.

The autoclave is closed, evacuated and filled with nitrogen. The evacuation and filling with nitrogen is repeated twice, then the autoclave is filled with CO, evacuated and refilled with CO. The evacuation and filling with CO is repeated twice.

The autoclave is subsequently pressurized with CO to a pressure of 120 bar and the mixture is heated to 100° C. while stirring. The reaction time is 20 hours. The mixture is subsequently cooled to room temperature, the autoclave is emptied and the organic phase is separated from the aqueous phase. The organic phase is filtered to remove traces of palladium and evaporated under reduced pressure, with the desired product being purified, if desired by crystallization or chromatography.

EXAMPLE 5b

Preparation of 5-chloro-2-hydroxyaniline

A degassed solution of 10 mmol of 5-chloro-2-hydroxynitrobenzene (starting material) and 40 ml of xylene are placed in an autoclave (volume: 200 ml). 0.125 mmol of BINAS (in the form of 0.72 g of an aqueous solution containing 0.173 mol of BINAS/kg of solution) as phosphine and 0.6 g (15 mmol) of NaOH, 41 ml of H$_2$O and 0.25 mmol of PdCl$_2$ are added. The pH is from 10 to 11.

The subsequent procedure is as described in Example 5a.

EXAMPLE 5c

Preparation of 5-chloro-2-hydroxyaniline

A degassed solution of 10 mmol of 5-chloro-2-hydroxynitrobenzene (starting material) and 40 ml of xylene are placed in an autoclave (volume: 200 ml). 0.125 mmol of ligand A (in the form of 1.25 g of an aqueous solution containing 0.1 mol of ligand A/kg of solution) as phosphine and 0.6 g (15 mmol) of NaOH, 41 ml of H$_2$O and 0.25 mmol of PdCl$_2$ are added. The pH is from 10.5 to 11.0.

The subsequent procedure is as described in Example 5a.

In comparison with Examples 5a and 5b, the ligand A used as phosphine leads to a significant increase in the yield, cf. also the table below.

EXAMPLE 6

Preparation of 3-aminostyrene

A degassed solution of 40 mmol of 3-nitrostyrene (starting material) and 40 ml of xylene are placed in an autoclave (volume: 200 ml). 2.0 mmol of BINAS (in the form of 11.56 g of an aqueous solution containing 0.173 mol of BINAS/kg of solution) as phosphine and 1.92 g (48 mmol) of NaOH, 23 ml of H$_2$O and 0.8 mmol of PdCl$_2$ are added. The pH is from 10.0 to 10.5.

The autoclave is closed, evacuated and filled with nitrogen. The evacuation and filling with nitrogen is repeated twice, then the autoclave is filled with CO, evacuated and refilled with CO. The evacuation and filling with CO is repeated twice.

The autoclave is subsequently pressurized with CO to a pressure of 120 bar and the mixture is heated to 100° C. while stirring. The reaction time is 20 hours. The mixture is subsequently cooled to room temperature, the autoclave is emptied and the organic phase is separated from the aqueous phase. The organic phase is filtered to remove traces of palladium and evaporated under reduced pressure, with the desired product being purified, if desired by crystallization or chromatography.

Explanations of the abbreviations TPPTS, BINAS and ligand A are given below.

TPPTS is a mixture of sodium salts of sulfonated triphenylphosphines and contains sodium salts of monosulfonated, disulfonated and trisulfonated triphenylphosphines. The preparation of such salts is described in DE 26 27 354.

BINAS refers to sodium salts of sulfonated 2.2'-bis(diphenylphosphinomethyl)-1,1'-binaphthalenes of the formula (A)

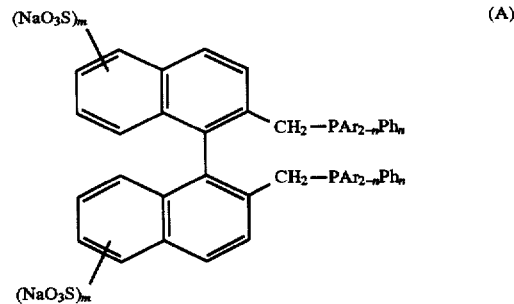

where Ar is m-C$_6$H$_4$SO$_3$Na and Ph is a phenyl radical, m are identical or different and each has the value 1 or 2 and n are identical or different and are each 0, 1 or 2.

The preparation of these salts or salt mixtures is described in EP 0 571 819.

Ligand A is a phosphine of the formula (B)

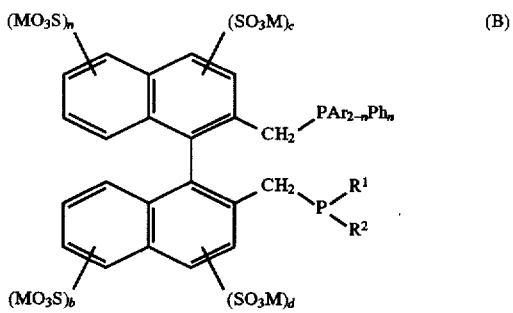

where M is Na, a, b, c and d are each 0 or 1, with the proviso that a+b+c+d is an integer from 1 to 4, Ar is a m-(NaSO$_3$)-C$_6$H$_4$ radical, n is 0, 1 or 2, Ph is a phenyl radical and R$^1$ and R$^2$ are each a cyclohexyl radical.

The preparation of this compound or a mixture of these compounds is described in the German Patent Application (file number 195 06 279.5) filed on the same day as the present patent application.

The results of the examples described above are shown in the table below.

The reactions described in the examples are essentially based on first experimental findings. Appropriate optimization of the reaction procedure should therefore enable the results, in particular the yields, to be improved further.

TABLE

| Example | Starting material | Phosphine | End product | Yield |
|---|---|---|---|---|
| 1a | 4-Cl-2-NO$_2$-benzaldehyde | TPPTS | 4-Cl-2-NH$_2$-benzaldehyde | 65% |
| 1b | | BINAS | | 70% |
| 2a | 4-Cl-3-CF$_3$-NO$_2$-benzene | TPPTS | 4-Cl-3-CF$_3$-NH$_2$-benzene | 45% |
| 2b | | BINAS | | 85% |
| 3a | 4-Cl-3-CN-NO$_2$-benzene | TPPTS | 4-Cl-3-CN-NH$_2$-benzene | 60% |
| 3b | | BINAS | | 60% |
| 4a | 4-Cl-NO$_2$-benzene | TPPTS | 4-Cl-NH$_2$-benzene | 40% |
| 4b | | BINAS | | 50% |
| 5a | 4-HO-3-Cl-NO$_2$-benzene | TPPTS | 4-HO-3-Cl-NH$_2$-benzene | 5% |
| 5b | | BINAS | | 10% |
| 5c | | Ligand A | | 50% |
| 6 | 3-NO$_2$-styrene | BINAS | 3-NH$_2$-styrene | 50% |

We claim:

1. A process for preparing aromatic amines, which comprises reacting an aromatic nitro compound with carbon monoxide in a solvent mixture comprising water and a water-insoluble organic solvent by means of a catalyst comprising palladium and a water-soluble phosphine under a pressure of from 5 to 300 bar and at a temperature of from 50 to 200° C., and separating the aqueous phase and the organic phase.

2. The process as claimed in claim 1, wherein the nitro compound used is a compound of the formula R$^1$R$_2$R$^3$ArNO$_2$, where R$^1$, R$^2$, R$^3$ are identical or different and are each hydrogen, an alkyl or alkoxy radical having from 1 to 6 carbon atoms, a halogenated alkyl radical having from 1 to 4 carbon atoms, a halogen, —OH —CHO, —CO—R$^4$, —CO$_2$R$^4$, —CONHR$_4$, —CON(R$^4$)$_2$, —SR$^4$, where R$^4$ is a radical having from 1 to 6 carbon atoms, —CN or —CH=CH—R$^5$, where R$^5$ is hydrogen or a radical having from 1 to 6 carbon atoms, and Ar is an aromatic radical.

3. The process as claimed in claim 1, wherein the aromatic nitro compound used is a compound R$^1$R$^2$R$^3$ArNO$_2$, where R$^1$, R$^2$ and R$^3$ are hydrogen, an alkyl or alkoxy radical having from 1 to 4 carbon atoms, a halogenated alkyl radical having 1 or 2 carbon atoms, a halogen, —OH, —CO—R$^4$ —CN or —CH=CH—R$^5$.

4. The process as claimed in claim 1, wherein the aromatic nitro compound used is a compound R$^1$R$^2$R$^3$ArNO$^2$, where at least one of the radicals R$^1$, R$^2$ and R$^3$ is a halogen, —OH, —CO—R$^4$, —CN or —CH=CH—R$^5$.

5. The process as claimed in claim 1, wherein the aromatic nitro compound used is a compound R$^1$R$^2$R$^3$ArNO$_2$, where one or two of the radicals R$^1$, R$^2$ and R$^3$ are a halogen, —OH, —CO—R$^4$, —CN or —CH=CH—R$^5$.

6. The process as claimed in claim 1, wherein the aromatic nitro compound used is a compound R$^1$R$^2$R$^3$ ArNO$_2$, where one or two of the radicals R$^1$, R$^2$ and R$^3$ are —Cl, —Br, —OH, —CO—R$^4$, where R$^4$ is an alkyl radical having from 1 to 4 carbon atoms or is a phenyl radical, —CN or —CH=CH—R$^5$, where R$^5$ is hydrogen, an alkyl radical having from 1 to 4 carbon atoms or a phenyl radical.

7. The process as claimed in claim 1, wherein the aromatic nitro compound used is a compound R$^1$R$^2$R$^3$ArNO$_2$, where Ar is an aromatic radical having from 6 to 20 carbon atoms.

8. The process as claimed in claim 1, wherein the aromatic nitro compound used is a compound R$^1$R$^2$R$^3$ArNO$_2$, where Ar is a phenyl, naphthyl, phenanthryl, biphenyl or binaphthyl radical.

9. The process as claimed in claim 1, wherein the aromatic nitro compound used is a compound R$^1$R$^2$R$^3$ArNO$_2$, where Ar is a phenyl, naphthyl or biphenyl radical.

10. The process as claimed in claim 1, wherein the aromatic nitro compound used is a compound R$^1$R$^2$R$^3$ArNO$_2$, where Ar is a phenyl radical.

11. The process as claimed in claim 1, wherein the water-insoluble organic solvent used is an aromatic hydrocarbon, an aliphatic hydrocarbon, a chlorinated aromatic or aliphatic hydrocarbon or a mixture thereof.

12. The process as claimed in claim 1, wherein palladium is used in the form of a water-soluble palladium salt.

13. The process as claimed in claim 1, wherein the water-soluble phosphine used is a phosphine containing —SO$_3$M groups, where M is hydrogen, ammonium, a monovalent metal or the equivalent of a polyvalent metal.

14. The process as claimed in claim 1, wherein a phosphine containing —SO$_3$M groups, where M is ammonium or an alkali metal is used.

15. The process as claimed in claim 1, wherein a triarylphosphine containing from 1 to 6 —SO$_3$M groups, where the aryl radicals are identical or different and are each phenyl or naphthyl, or a mixture of such triarylphosphines, is used.

16. The process as claimed in claim 1, wherein a triphenylphosphine containing from 1 to 3 —SO₃M groups is used.

17. The process as claimed in claim 1, wherein the phosphine used is one of the formula (A)

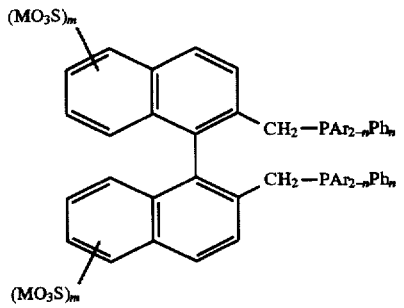

(A)

where Ar is m-C₆H₄SO₃M, M is hydrogen, ammonium, a monovalent metal or the equivalent of a polyvalent metal and Ph is a phenyl radical, m are identical or different and each have the value 1 or 2 and n are identical or different and are each 0, 1 or 2, or a mixture of such phosphines.

18. The process as claimed in claim 1, wherein the phosphine used is one of the formula (B)

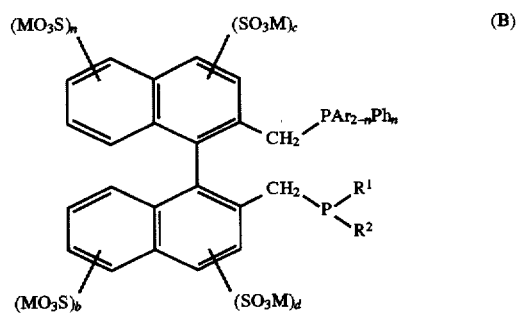

(B)

where M is hydrogen, ammonium, a monovalent metal or the equivalent of a polyvalent metal, a, b, c and d are each 0 or 1, with the proviso that a+b+c+d is an integer from 1 to 4, Ar is a m-(MSO₃)-C₆H₄ radical and M is as defined above, n is 0, 1 or 2, Ph is a phenyl radical, $R^1$ and $R^2$ are identical or different and are each an alkyl radical having from 1 to 10 carbon atoms or a cycloaliphatic radical having from 5 to 10 carbon atoms in the ring, or a mixture of such phosphines.

19. The process as claimed in one or more of claim 1, wherein a phosphine of the formula (B) where $R^1$ and $R^2$ are each a cyclohexyl radical is used.

20. The process as claimed in claim 12, wherein the palladium salt is PdCl₂, Pd(NO₃)₂, Pd(acetate)₂ or PdSO₄.

21. The process as claimed in claim 14, wherein M is sodium or potassium.

22. The process as claimed in claim 15, wherein the triarylphosphine contains from 1 to 3 —SO₃M groups.

* * * * *